United States Patent
Hemmert

(10) Patent No.: US 9,162,069 B2
(45) Date of Patent: Oct. 20, 2015

(54) TEST METHOD FOR COCHLEAR IMPLANT STIMULATION STRATEGIES

(71) Applicant: MED-EL Elektromedizinische Geraete GmbH, Innsbruck (AT)

(72) Inventor: Werner Hemmert, Garching (DE)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 14/102,564

(22) Filed: Dec. 11, 2013

(65) Prior Publication Data

US 2014/0100630 A1 Apr. 10, 2014

Related U.S. Application Data

(63) Continuation of application No. PCT/US2012/046163, filed on Jul. 11, 2012.

(60) Provisional application No. 61/506,287, filed on Jul. 11, 2011.

(51) Int. Cl.
*A61N 1/08* (2006.01)
*A61N 1/372* (2006.01)
*A61N 1/36* (2006.01)
*G10L 15/02* (2006.01)

(52) U.S. Cl.
CPC ........ *A61N 1/37252* (2013.01); *A61N 1/36032* (2013.01); *G10L 15/02* (2013.01); *A61N 1/37241* (2013.01)

(58) Field of Classification Search
CPC .......... A61N 1/37252; A61N 1/36032; A61N 1/37241
USPC ................. 607/55, 56, 57, 137; 704/200, 256
See application file for complete search history.

(56) References Cited

U.S. PATENT DOCUMENTS

| | | | |
|---|---|---|---|
| 5,963,904 A * | 10/1999 | Lee et al. | 704/254 |
| 6,289,247 B1 * | 9/2001 | Faltys et al. | 607/57 |
| 2008/0119910 A1 * | 5/2008 | Daly et al. | 607/57 |
| 2009/0018615 A1 | 1/2009 | Blamey et al. | |

(Continued)

OTHER PUBLICATIONS

Holmberg et al, "Speech encoding in a model of peripheral auditory processing: Quantitative assessment by means of automatic speech recognition." *Speech Communication* 49.12 (2007): 917-932.

Wang et al, "Auditory information coding by modeled cochlear nucleus neurons." *Journal of computational neuroscience* 30.3 (2011): 529-542.

(Continued)

*Primary Examiner* — Christopher D Koharski
*Assistant Examiner* — Michael Carey
(74) *Attorney, Agent, or Firm* — Sunstein Kann Murphy & Timbers LLP

(57) ABSTRACT

An arrangement and method for hearing implant signal processing is described. A hearing implant signal processor converts a speech signal input into multi-channel electrical stimulation signals for a cochlear implant electrode array. A feature adjustment module adjusts feature resolution of the electrical stimulation signals to produce a corresponding sequence of cochlear stimulation feature vectors. A speech recognition vector pre-processor maps the cochlear stimulation feature vectors into corresponding speech recognition feature vectors. A speech recognition engine evaluates the speech recognition features vectors with probabilistic state sequence models to produce speech recognition outputs corresponding to the speech signal input.

16 Claims, 3 Drawing Sheets

(56) References Cited

U.S. PATENT DOCUMENTS

| | | |
|---|---|---|
| 2009/0024183 A1 | 1/2009 | Fitchmun |
| 2009/0312820 A1* | 12/2009 | Nie et al. .......... 607/57 |
| 2010/0131262 A1* | 5/2010 | Gruhn et al. ......... 704/8 |
| 2010/0185261 A1* | 7/2010 | Schleich ........... 607/57 |
| 2010/0191308 A1 | 7/2010 | Meister |

OTHER PUBLICATIONS

International Searching Authority, Authorized Officer Blaine R. Copenheaver, International Search Report and Written Opinion—PCT/US2012/046163, date of mailing Sep. 27, 2012, 11 pages.

Extended European Search Report—European Patent Application 12810994.9, dated Dec. 2, 2014, 8 pages.

\* cited by examiner

TEST METHOD FOR COCHLEAR IMPLANT STIMULATION STRATEGIES

This application is a continuation of co-pending Patent Cooperation Treaty Application PCT/US2012/046163, filed Jul. 11, 2012, which in turn claims priority from U.S. Provisional Patent Application 61/506,287, filed Jul. 11, 2011, which are incorporated herein by reference in their entireties.

TECHNICAL FIELD

The present invention relates to cochlear, auditory brainstem, midbrain or cortical implants and evaluation of their signal coding strategies.

BACKGROUND ART

A normal ear transmits sounds as shown in FIG. 1 through the outer ear 101 to the tympanic membrane (eardrum) 102, which moves the bones of the middle ear 103, which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar where the spiral ganglion cells of the acoustic nerve 113 reside. In response to received sounds transmitted by the middle ear 103, the fluid filled cochlea 104 functions as a transducer to generate electric pulses that are transmitted to the cochlear nerve 113, and ultimately to the brain. Hearing is impaired when there are problems in the ability to transduce external sounds into meaningful action potentials along the neural substrate of the cochlea 104.

In some cases, hearing impairment can be addressed by a cochlear implant (CI), a brainstem-, midbrain- or cortical implant that electrically stimulates nerve tissue with small currents delivered by multiple electrode contacts distributed along an implant electrode. For cochlear implants, the electrode array is inserted into the cochlea. For brain-stem, midbrain and cortical implants, the electrode array is located in the auditory brainstem, midbrain or cortex, respectively. FIG. 1 shows some components of a typical cochlear implant system where an external microphone provides an audio signal input to an external signal processor 111 which implements one of various known signal processing schemes. For example, signal processing approaches that are well-known in the field of cochlear implants include continuous interleaved sampling (CIS) digital signal processing, channel specific sampling sequences (CSSS) digital signal processing (as described in U.S. Pat. No. 6,348,070, incorporated herein by reference), spectral peak (SPEAK) digital signal processing, and compressed analog (CA) signal processing. The processed signal is converted by the external signal processor 111 into a digital data format, such as a sequence of data frames, for transmission into a receiving stimulator processor 108. Besides extracting the audio information, the receiver processor in the stimulator processor 108 may perform additional signal processing such as error correction, pulse formation, etc., and produces a stimulation pattern (based on the extracted audio information) that is sent through electrode lead 109 to an implanted electrode array 110. Typically, the electrode array 110 includes multiple stimulation contacts on its surface that provide selective electrical stimulation of the cochlea 104.

Improving coding strategies for cochlear implants requires speech perception tests with large numbers of patients, which are very time demanding and depend to a large extend on the individuals. If changes involve new hardware features of the implant, these tests are not possible before the new devices are implanted. Performance improvements are difficult to prove, they require subjective speech tests with large numbers of cochlear implant patients.

SUMMARY

Embodiments of the present invention are directed to an arrangement and corresponding method for cochlear implant signal processing. A cochlear implant signal processor converts a speech signal input into multi-channel electrical stimulation signals for a cochlear implant electrode array. A feature adjustment module adjusts feature resolution of the electrical stimulation signals to produce a corresponding sequence of cochlear stimulation feature vectors. A speech recognition vector pre-processor maps the cochlear stimulation feature vectors into corresponding speech recognition feature vectors. A speech recognition engine evaluates the speech recognition features vectors with probabilistic state sequence models to produce speech recognition outputs corresponding to the speech signal input.

In further specific embodiments, there may be a cochlear field distribution model for modeling field distributions at spatial locations within the cochlea to modify the electrical stimulation signals to reflect crosstalk between channels. There also may be an auditory nerve excitation model for modeling neural responses at spatial locations within the cochlea to modify the electrical stimulation signals to reflect nerve action potentials of the auditory nerve. In addition, there may be a cochlear nucleus response model or/and models of further neuronal processing stages for modeling if and how information from electrically evoked auditory nerve spike trains is transmitted to the cortex. In the case of brainstem implants, a model of the electrical excitation of brainstem neurons, and in the case of mid-brain implants, a model of the electrical excitation of midbrain neurons and in the case of cortical implants, a model of the electrical excitation of cortical neurons—and the following higher neuronal processing stages—may be used to derive features for the automatic speech recognition system.

The feature adjustment module may adjust the feature resolution of the electrical stimulation signals to reduce temporal and/or spectral resolution of the electrical stimulation signals. And the speech recognition vector pre-processor may be a multi-layer perceptron.

DETAILED DESCRIPTION

Various embodiments of the present invention are directed to arrangements for testing and optimizing coding strategies of cochlear implants by replacing patient tests with models of neuronal excitation in the inner ear and evaluating these with a properly adapted automatic speech recognition (ASR) system. From an ASR perspective, multi-channel cochlear implant electrical stimulation signals and/or modeled neuronal spike trains can be thought of as speech signals with unconventional features that can be adapted for use by a properly optimized ASR engine and speech model database arrangement. This allows quantitative evaluation of different cochlear implant stimulation signal coding strategies under many different complex and realistic evaluation conditions including adverse acoustic conditions such as with noise and/or reverberation. The test results may include a detailed report on recognition errors (such as which phonemes are more likely to be confused) which in turn allows potential weaknesses in coding strategies to be identified and fixed.

Figure 1:
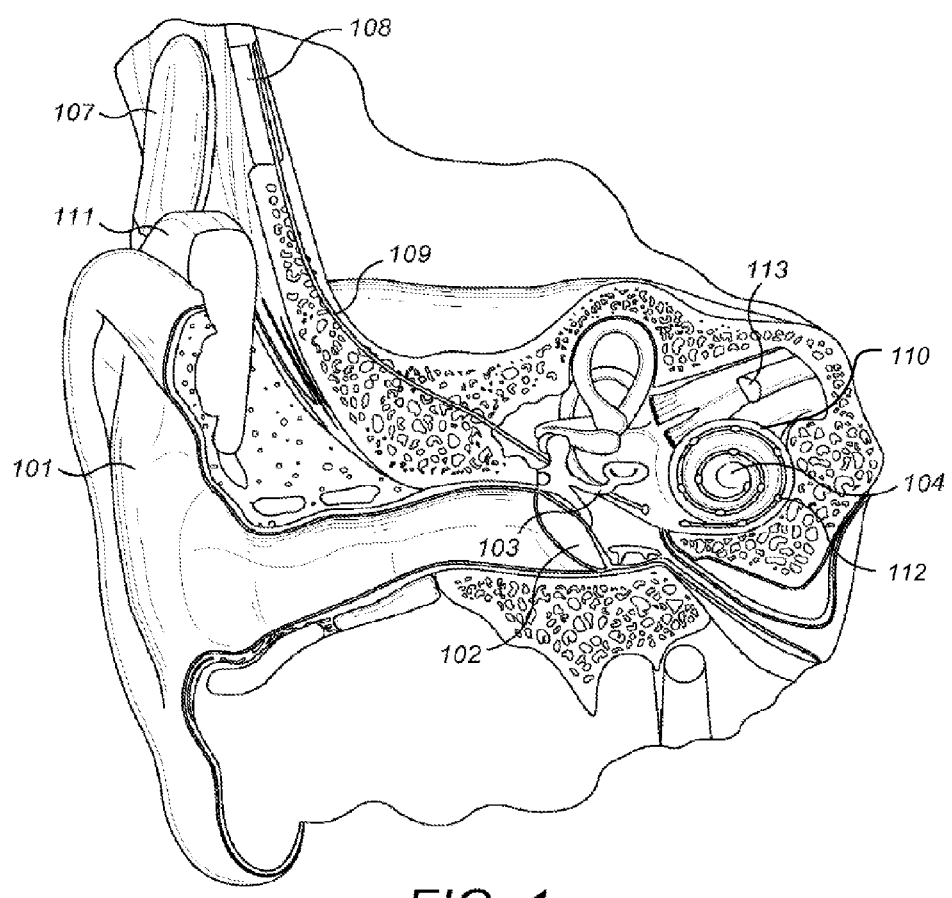
FIG. 1 shows various anatomical structures of a typical human ear and a cochlear implant system.
Figure 2:
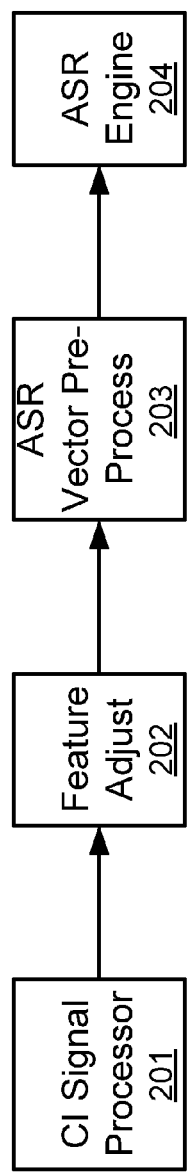
FIG. 2 shows various functional blocks in a cochlear implant signal processing arrangement according to an embodiment of the present invention.

FIG. 2 shows various functional blocks in a cochlear implant signal processing arrangement according to an embodiment of the present invention. A CI signal processor 201 converts speech signal inputs into multi-channel electrical stimulation signals for a cochlear implant electrode array. The arrangement shown in FIG. 2 specifically investigates the coding of speech-relevant information by the CI signal processor 201 only.

A feature adjustment module 202 adjusts feature resolution of the electrical stimulation signals from the CI signal processor 201 to produce a corresponding sequence of cochlear stimulation feature vectors for speech recognition processing. For example, the feature adjustment module 202 typically may adjust the feature resolution of the electrical stimulation signals to reduce temporal resolution of the electrical stimulation signals as needed for speech recognition. Specifically, the feature adjustment module 202 may rectify the electrical stimulation signal and down-sample (convolve) the signal with a Hanning window. Such a Hanning window might typically be 25 msec long and advanced in 10 msec steps to yield representative cochlear stimulation feature vectors every 10 msec. The features are typically complemented by their first and second time derivatives (also known as delta- and double delta-features), for example, based on a well-known ASR approach such as SPRACHcore.

A speech recognition vector pre-processor 203 maps the cochlear stimulation feature vectors from the feature adjustment module 202 into corresponding speech recognition feature vectors. This reflects that the speech recognition system itself has its own optimal number of input channels (usually about 12) where its recognition performance reaches some best level of performance. For a meaningful comparison of different cochlear implant signal coding strategies, it is helpful to keep constant the number of features that are fed into the recognizer. There a number of well-known approaches for doing this, including without limitation discrete cosine transform (DCT), principal component analysis (PCA), linear discriminant analysis (LDA), Karhunen-Loève-Transformation (KLT), multi-layer perceptron (MLP), a support vector machine (SVM).

A speech recognition engine 204 evaluates the speech recognition features vectors from the speech recognition vector pre-processor 203 with probabilistic state sequence models (e.g., hidden Markov models (HMMs) to produce speech recognition outputs corresponding to the speech signal input to the CI signal processor 201.

In some cases the spectral dimensionality of the electrical stimulation signals from the CI signal processor 201 may be relatively high (e.g. if there are much more than 12 frequency bands) and the feature adjustment module 202 may reduce the frequency resolution of the electrical stimulation signals as well as the temporal resolution. As in the time-domain, down-sampling can be applied, for example, with overlapping Hanning windows. Alternatively a discrete cosine transform (DCT) may transform the spectral features and only the first 12 coefficients (and their deltas and double deltas) are fed into the recognition back-end of the speech recognition vector pre-processor 203 and the speech recognition engine 204.

Figure 3:
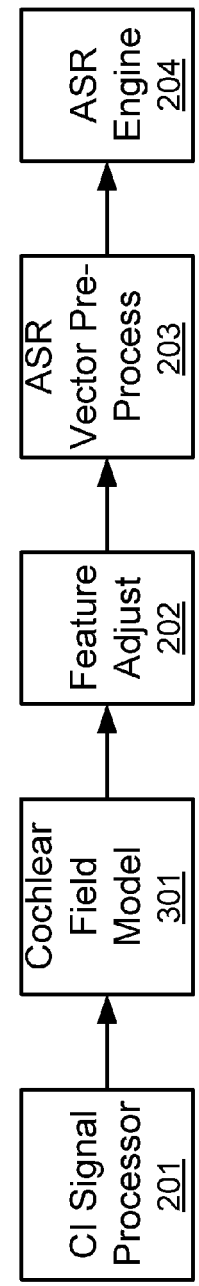
FIG. 3 shows various functional blocks in a cochlear implant signal processing arrangement according to another embodiment of the present invention.

Besides a basic evaluation of the CI signal processor 201 electrical stimulation signal coding, embodiments of the present invention also are useful for taking into account the reactions of the neural pathways involved in the brain processing the electrical stimulation signals. For example, the field distribution of the applied stimulation signal is responsible for crosstalk between CI channels and limits the number of effective channels which can be separated by the implant patients. So a cochlear field distribution model 301 as shown in FIG. 3 may be used to model field distributions at spatial locations within the cochlea to modify the electrical stimulation signals to reflect crosstalk between channels. It may be useful to use multiple different cochlear field distribution models 301 of different geometrical detail and/or different phenomenological approaches to describe the spread of excitation measured by the CI or which is measured in psychophysical experiments. For example, cochlear field distribution models 301 may be used to represent the excitation for many locations along the cochlea (e.g. 100-3600).

Figure 4:
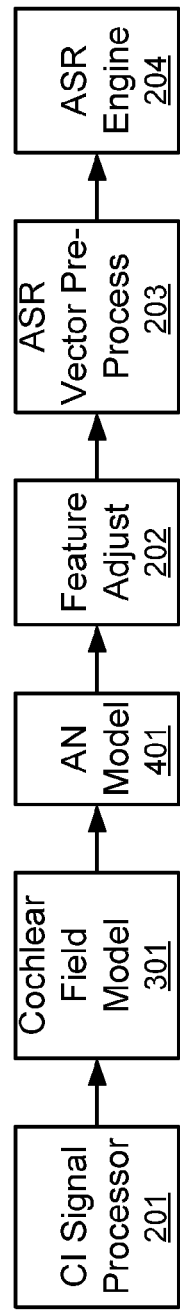
FIG. 4 shows various functional blocks in a cochlear implant signal processing arrangement according to another embodiment of the present invention.

In addition or alternatively, embodiments of the present invention may model the conversion of the electrical stimulation signal into nerve-action potentials of the auditory nerve. Thus an auditory nerve excitation model 401 as shown in FIG. 4 may be used to model neural responses at spatial locations within the cochlea to modify the electrical stimulation signals to reflect nerve action potentials of the auditory nerve. This process is very nonlinear and may destroy a significant part of the information provided by the cochlear implant. Therefore it can be very useful to apply appropriate and precise auditory nerve excitation models 401 of the excitation of the auditory nerve to process the signal features which are suitable for the evaluation with automatic speech recognition. For example, this may involve computing responses of a large number of auditory nerve fibers along the cochlea (e.g., 100-30.000).

Figure 5:
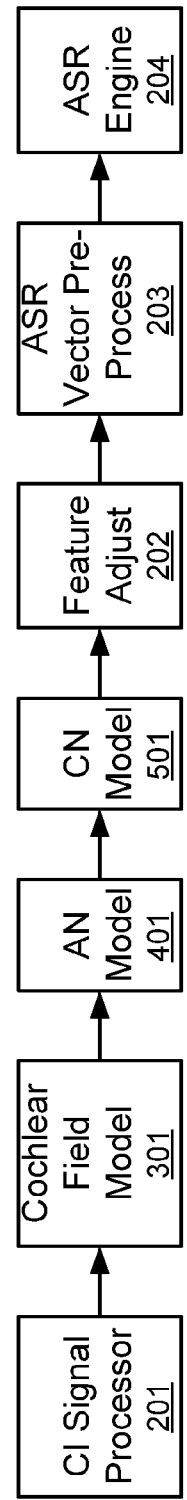
FIG. 5 shows various functional blocks in a cochlear implant signal processing arrangement according to another embodiment of the present invention.

An extension to the previous embodiment can include a model of the next processing stage in the auditory brainstem, the cochlear nucleus (CN). Thus a cochlear nucleus response model 501 as shown in FIG. 5 may be used to model discharge trains of CN neurons to electrically stimulated auditory nerve excitation. (the model 501 might also include the next higher processing stages) As the discharge trains of the electrically stimulated auditory nerve are unnatural, it is likely that information is also lost in the synapses and/or the neurons especially in the first neuronal processing stage(s).

Using automatic speech recognition to evaluate cochlear implant signal processing allows the design of various complex but realistic test scenarios such as clear speech, speech in noise, and/or speech in reverberating rooms. The generalization capacity of contemporary ASR systems is somewhat limited, but for these purposes it is not necessary to optimize the speech recognition per-se. The mismatch between test and training conditions can be reduced in steps such as by limiting the size of the recognition vocabulary, including noise in the training data, and/or using a single speaker corpus instead of multiple speakers. For example, a speech corpus such as the ISOLET database consisting of examples the spoken alphabet is short and there is also a noisy version available. Special speech corpora such as Fletcher's consonant-vowel-consonant (CVC) syllables allow the investigation of vowel or consonant confusion. A rich speech corpus like TIMIT provides a large dataset including the analysis of many vowel and/or consonant confusions.

Noise/reverberation can be added to a clean speech corpora, or noisy corpora/corpora recorded in reverberating rooms can be used. Speech recognition systems have a hard time classifying noisy speech, but this may be addressed at least in part by performing matched tests which include the same (but usually not identical) noise in training and testing. In this case, the ASR engine is trained and tested for various acoustic conditions (signal-to-noise ratio, reverberation, etc.). A further reduction in recognizer mismatch can be achieved if the training corpus and the test corpus are from the same speaker. As the speech recognition backend, ASR systems such as HTK are available, and most preprocessing tools are available for example in the SPRACHcore system.

Embodiments of the present invention such as those discussed above allow a quantitative evaluation of novel CI stimulation signal coding strategies before the device is implanted in patients or even before it is fabricated. These arrangements are fast and can enable speeding-up of innovation cycles by orders of magnitude. However, current ASR systems rely strongly on spectral features, and it may be that humans can process fine-grained temporal information which is usually not exploited in recognition strategies. Temporal information also can be made available to ASR systems, for example in the form of inter-peak interval histograms (IPIH), average localized synchrony detection (ALSD). Moreover, the exact pathology of human cochlear implant patients is not entirely known and models of neuronal excitation may be only approximate. So there is likely to still be a place for psychophysical tests.

Embodiments of the invention may be implemented in whole or in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. An arrangement for cochlear implant signal processing, the arrangement comprising:
   a cochlear implant signal processor configured for converting a speech signal input into multi-channel electrical stimulation signals for a cochlear implant electrode array;
   a feature adjustment module coupled to the signal processor and configured for adjusting feature resolution of the electrical stimulation signals to produce a corresponding sequence of cochlear stimulation feature vectors;
   a speech recognition vector pre-processor coupled to the feature adjustment module and configured for mapping the cochlear stimulation feature vectors into corresponding speech recognition feature vectors; and
   a speech recognition engine coupled to the speech recognition vector pre-processor and configured for evaluating the speech recognition features vectors with a plurality of probabilistic state sequence models to produce speech recognition outputs corresponding to the speech signal input.

2. An arrangement according to claim 1, further comprising:
   a cochlear field distribution model coupled to the signal processor and configured for modeling field distributions at spatial locations within the cochlea to modify the electrical stimulation signals to reflect crosstalk between channels.

3. An arrangement according to claim 1, further comprising:
   an auditory nerve excitation model coupled to the signal processor and configured for modeling neural responses at spatial locations within the cochlea.

4. An arrangement according to claim 1, further comprising:
   a neural response model coupled to the signal processor and configured for modeling discharge trains of auditory neurons to electrically stimulated auditory nerve responses.

5. An arrangement according to claim 1, wherein the speech recognition vector pre-processor is further configured to extract temporal features from the cochlear stimulation feature vectors for the speech recognition engine.

6. An arrangement according to claim 1, wherein the feature adjustment module is further configured to adjust the feature resolution of the electrical stimulation signals to reduce temporal resolution of the electrical stimulation signals.

7. An arrangement according to claim 1, wherein the feature adjustment module is further configured to adjust the feature resolution of the electrical stimulation signals to reduce spectral resolution of the electrical stimulation signals.

8. An arrangement according to claim 1, wherein the speech recognition vector pre-processor is a multi-layer perceptron.

9. A method for cochlear implant signal processing, the method comprising:
- converting a speech signal input into multi-channel electrical stimulation signals for a cochlear implant electrode array;
- adjusting feature resolution of the electrical stimulation signals to produce a corresponding sequence of cochlear stimulation feature vectors;
- mapping the cochlear stimulation feature vectors into corresponding speech recognition feature vectors; and
- evaluating the speech recognition features vectors with a plurality of probabilistic state sequence models to produce speech recognition outputs corresponding to the speech signal input.

10. A method according to claim 9, further comprising:
modeling field distributions at spatial locations within the cochlea to modify the electrical stimulation signals to reflect crosstalk between channels.

11. A method according to claim 9, further comprising:
modeling discharge trains of electrically stimulated auditory nerve tissue at spatial locations within the cochlea.

12. A method according to claim 9, further comprising:
modeling neural responses of auditory neural tissue to electrical stimulation of the auditory nerve.

13. A method according to claim 9, further comprising:
extracting temporal features from the cochlear stimulation feature vectors for the speech recognition engine.

14. A method according to claim 9, wherein adjusting the feature resolution of the electrical stimulation signals includes reducing temporal resolution of the electrical stimulation signals.

15. A method according to claim 9, wherein adjusting the feature resolution of the electrical stimulation signals includes reducing spectral resolution of the electrical stimulation signals.

16. A method according to claim 9, wherein mapping the cochlear stimulation feature vectors is based on using a multi-layer perceptron.

* * * * *